United States Patent
Summers et al.

(10) Patent No.: US 6,797,966 B2
(45) Date of Patent: Sep. 28, 2004

(54) QUICK-INSTALL IRRADIATION UNIT AND METHOD OF MAKING SAME

(75) Inventors: George Robert Summers, Carleton Place (CA); Forwood Cloud Wiser, III, Kingston, NJ (US)

(73) Assignee: Engineering Dynamics, Ltd., Ontario (CA)

( * ) Notice: Subject to any disclaimer, the term of this patent is extended or adjusted under 35 U.S.C. 154(b) by 400 days.

(21) Appl. No.: 09/770,700

(22) Filed: Jan. 26, 2001

(65) Prior Publication Data

US 2002/0100878 A1 Aug. 1, 2002

(51) Int. Cl.[7] .............................. A61L 2/10; A61L 9/20
(52) U.S. Cl. .............. 250/492.1; 250/436; 250/454.11; 250/455.11; 250/504 R; 422/24; 422/121
(58) Field of Search ............................. 250/492.1, 436, 250/454.11, 455.11, 504 R, 435; 422/24

(56) References Cited

U.S. PATENT DOCUMENTS

| | | | |
|---|---|---|---|
| 2,381,452 A | 8/1945 | Hrabak | 250/88 |
| 4,458,872 A * | 7/1984 | Couch | 248/497 |
| 4,896,042 A | 1/1990 | Humphreys | 250/435 |
| 5,330,722 A | 7/1994 | Pick et al. | 422/121 |
| 5,635,133 A * | 6/1997 | Glazman | 422/24 |
| 5,817,276 A * | 10/1998 | Fencl et al. | 422/24 |
| 5,837,207 A | 11/1998 | Summers | 422/121 |
| 5,894,130 A | 4/1999 | Bach | 250/436 |

* cited by examiner

Primary Examiner—Jack I. Berman
(74) Attorney, Agent, or Firm—Pearne & Gordon LLP

(57) ABSTRACT

A quick-install irradiation unit for irradiating a surface includes an adapter that accepts a frame for supporting an ultraviolet lamp with a reflector or a lens for focusing the radiation on the surface. The unit may include a housing secured to one end of the frame containing a drive motor and a cam assembly which oscillate the reflector, if the radiation is focused on a predefined area of the surface at any given time. The unit can be quickly installed in any orientation on practically any flat surface.

16 Claims, 7 Drawing Sheets

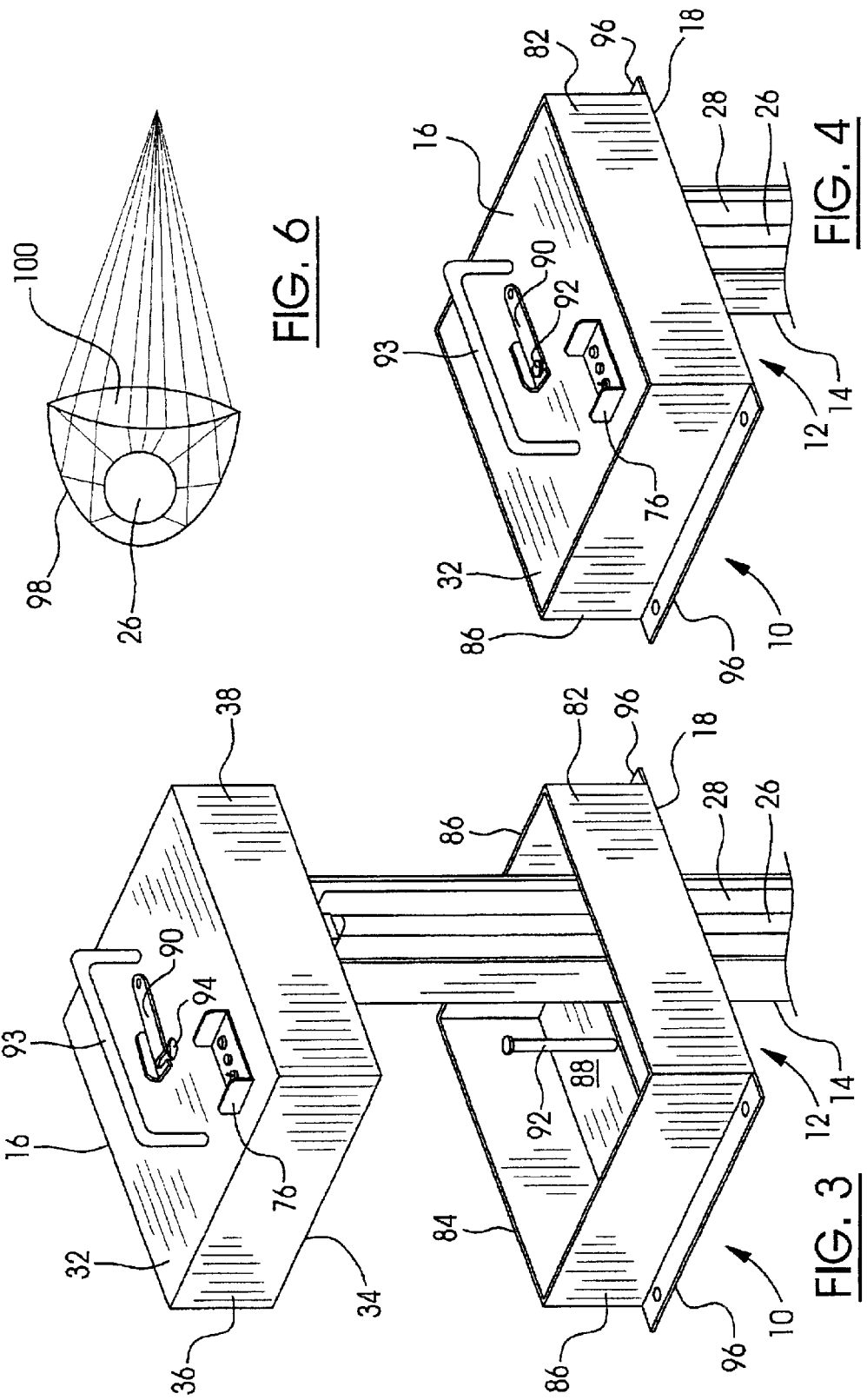

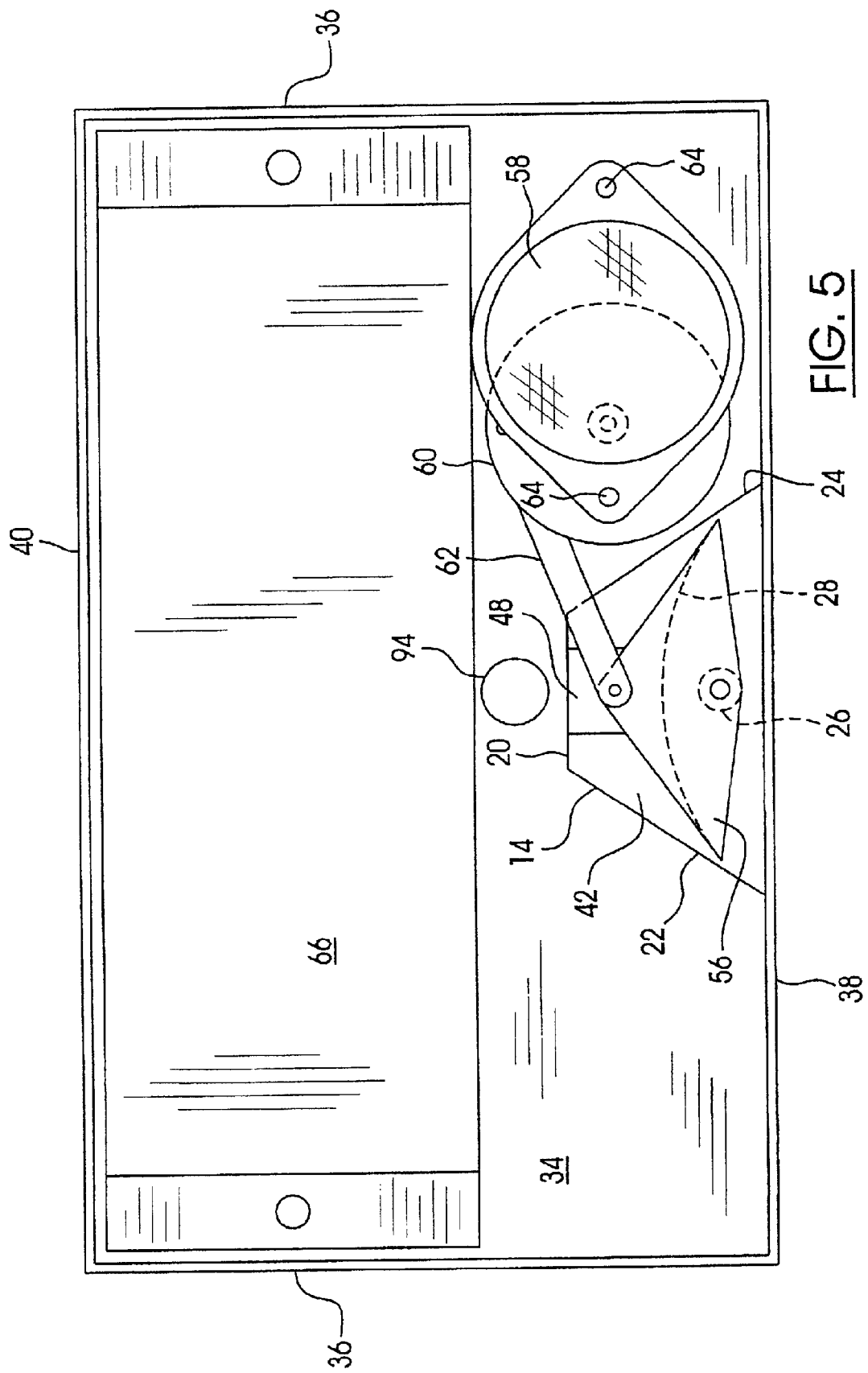

QUICK-INSTALL IRRADIATION UNIT AND METHOD OF MAKING SAME

TECHNICAL FIELD

The present invention relates to irradiation devices for controlling airborne micro-organisms and, in particular, to a quick-install germicidal irradiation unit for destroying micro-organisms collected on a surface irradiated by the unit.

BACKGROUND OF THE INVENTION

The airborne transmission of disease organisms, especially respiratory disease organisms, has long been recognized as a serious problem. Health care authorities and biologists have now become acutely aware of the problem due to the evolution of antibiotic resistant strains of streptococcus and tuberculosis, for example. It is well known that many diseases caused by both bacteria and viruses are primarily transmitted from host to host by air currents. Therefore, germicidal air filters have been invented and have proven to be effective in removing microorganisms from the air and destroying them. Examples of such filters are described in U.S. Pat. No. 5,330,722 which issued on Jul. 19, 1994 to Pick and has subsequently been assigned to the applicant. The germicidal air filtration systems described in that patent are principally suitable for permanent or semi-permanent installations.

As another example, a portable germicidal air filter is described in U.S. Pat. No. 5,837,207, which issued on Nov. 17, 1998 to Summers and also assigned to the applicant. The light weight portable germicidal air filter for home and personal use described in that patent includes a cabinet that houses an electrostatic air filter, an ultraviolet lamp and a parabolic reflector or a convex lens for focusing the ultraviolet radiation emitted by the lamp on an upstream side of the air filter. The reflector or the lamp with the lens is constantly oscillated to systematically sweep the upstream side of the filter with germicidal levels of radiation. A fan adjacent the downstream side of the filter draws air through the filter and impels it out through air outlets in the side walls of the cabinet.

It is also known to install stationary unshielded ultraviolet lamps in air ducts of commercial and domestic heating systems, as taught, for example, in U.S. Pat. No. 5,894,130, which issued to Bach on Aug. 13, 1999. Such devices are installed downstream of air filters on the theory that short, high-intensity exposure to ultraviolet light as air is drawn past the ultraviolet lamps will destroy at least a proportion of the microorganisms suspended in the air. A principal disadvantage of such systems is that the unshielded lamps readily collect airborne dust, which rapidly reduces their effectiveness. A further disadvantage is that as velocity of air flow changes due to various operating stages of the air handling system, the efficacy of the treatment changes. Another disadvantage is that areas known to support the reproduction of micro-organisms, such as air filters and air conditioning coils are untreated.

Air handling systems without germicidal radiation are still widely used in many applications. For example, most domestic forced-air heating systems have a filter pad installed in the return air path to remove suspended particulate matter from the air. Micro-organisms on the particulate matter collected on the filter pad are not destroyed and may, in fact, reproduce. A proportion of the particulate matter collected on the filter pad is re-suspended in air when the filter pad is replaced, releasing the micro-organisms again. Studies have also shown that the filter pads are not the only place that supports the growth and reproduction of micro-organisms. A warm and moist environment such as air conditioning and refrigerator coils and ducts surrounding such coils are known to provide a suitable environment for many types of micro-organisms, including fungus and mold.

Therefore, there exists a need for a quick-install irradiation unit adapted to be conveniently installed in proximity to a surface that collects or supports growth of micro-organisms, to expose that surface to germicidal levels of radiation.

SUMMARY OF THE INVENTION

It is an object of the invention to provide a quick-install irradiation unit for irradiating a surface.

It is another object of the invention to provide a quick-install irradiation unit that is adapted to be quickly and conveniently installed in proximity to a surface to be irradiated, regardless of an installed orientation of the unit.

It is a further object of the invention to provide a quick-install irradiation unit that is simple to construct, inexpensive to manufacture and easy to install.

These and other objects of the invention are realized in a quick-install irradiation unit for irradiating a surface, which comprises at least one radiation source and means for focusing radiation emitted by the source. A generally elongated support frame is provided for operatively securing the radiation source and means for focusing, to form a quick-install unit adapted to be mountable at only one end thereof. A mounting bracket is provided for mounting the one end of the germicidal unit in proximity to the surface so that the field is coincident with the surface and the surface is exposed to radiation.

The quick-install irradiation unit in accordance with the invention preferably comprises a support structure including an elongated frame and a housing secured to one end of the frame. A mounting bracket adapted to be mounted to a structure supporting the surface to be irradiated receives the housing. The mounting bracket supports the elongated frame in proximity to the surface. At least one ultraviolet radiation source is supported by the elongated frame for exposing at least a portion of the surface to the ultraviolet radiation. If the means for focusing the ultraviolet radiation emitted by the source focuses the radiation in a narrow, concentrated band, it is supported on opposite ends of the elongated frame, and rotatable about the source so that a predefined area of the surface is exposed to the focused ultraviolet radiation at any given time. The focusing means is oscillated by a motor supported within the housing and operatively connected to the rotatable means for focusing, so that the surface is systematically exposed to radiation. The germicidal irradiation unit further comprises means for detachably locking the housing to the mounting bracket.

The focusing of the ultraviolet radiation may be accomplished by a reflector positioned behind an ultraviolet lamp. The reflector is shaped to focus the radiation emitted by the radiation source on a predetermined area. If the reflector is mounted in a stationary position, the reflector is shaped to focus the radiation on the entire area. If, however, the reflector is rotatably mounted, it is preferably shaped to focus the radiation in a narrow, concentrated band on the surface to be irradiated. Alternatively, the radiation may be focused by a reflector behind the lamp in combination with an elongated lens positioned in front of the lamp, so that substantially all of the ultraviolet radiation emitted by the ultraviolet source is focused in a relatively narrow, elongated band on the surface to be irradiated. The means for focusing the radiation, e.g. a reflector or elongated lens, may be oscillated about an axis parallel to the axis of the radiation source by an electric motor, for example, which drives a cam shaft assembly at a predefined rate to effect the desired irradiation of the surface.

The germicidal irradiation unit in accordance with the invention includes very few components and the components are light in weight, and the unit is equipped with a separable mounting bracket. The germicidal irradiation unit is therefore easily handled, and may be quickly and conveniently installed, for example, in an air filter or a heating system to irradiate a filter pad, or any other supporting structures in a desired orientation and proximity to a surface to be irradiated.

BRIEF DESCRIPTION OF THE DRAWINGS

Further features and advantages of the present invention will become apparent from the following detailed description, taken in combination with the appended drawings, in which:

FIG. 3 is a perspective view of the embodiment shown in FIG. 1, illustrating a condition in which the housing is withdrawn from the mounting bracket;

FIG. 4 is a perspective view of the embodiment shown in FIG. 1, illustrating a condition in which the housing is received in the mounting bracket and locked in place;

FIG. 5 is a top plan view of the embodiment shown in FIG. 1, with a top plate of the housing removed to illustrate components contained in the housing;

FIG. 6 is a schematic view showing an alternate arrangement for focusing the ultraviolet radiation in which a lens and reflector combination focus the radiation on a surface;

It will be noted that throughout the appended drawings, like features are identified by like reference numerals.

DETAILED DESCRIPTION OF THE PREFERRED EMBODIMENT

Figure 1:
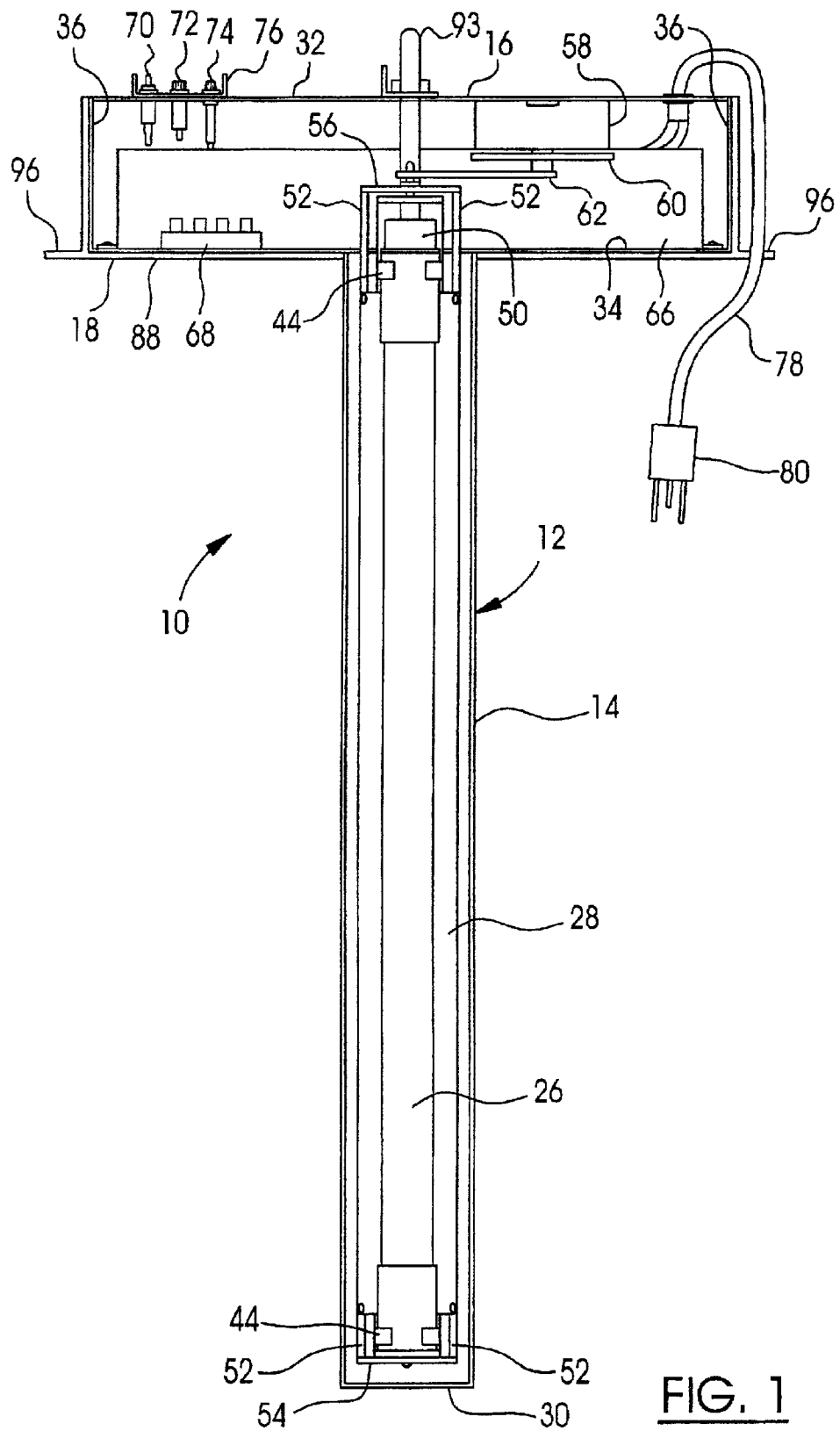
FIG. 1 is a front elevational view of a preferred embodiment of the invention, with front walls of a mounting bracket and housing removed to illustrate components contained in the housing.

FIGS. 1 through 4 illustrate a preferred embodiment of a quick-install irradiation unit in accordance with the invention, which is generally indicated by reference numeral 10. The irradiation unit 10 includes a support structure 12 that includes an elongated frame 14 and a rectangular housing 16 secured to one end of the frame 14. A mounting bracket 18 is adapted to be mounted to a flat surface, such as a side of a heating or cooling duct, furnace, air conditioner, or other air handling equipment (not shown). The mounting bracket is conveniently rectangular and removably receives the housing 16 to permit a quick and convenient installation of the irradiation unit 10 to the flat surface. The elongated frame 14 is constructed using sheet metal, for example.

Figure 2:
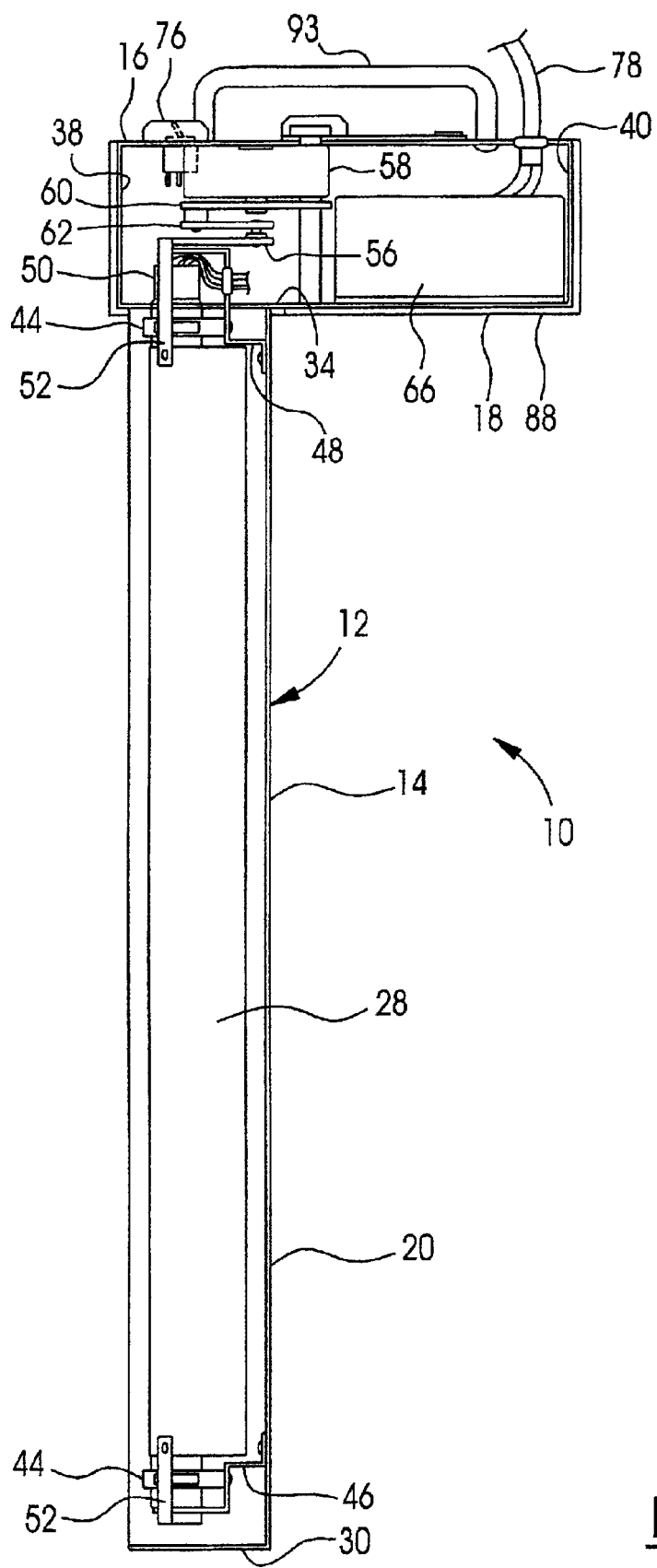
FIG. 2 is a side elevational view of the embodiment shown in FIG. 1, with side walls of the mounting bracket and the housing removed to illustrate components contained in the housing.

As more clearly shown in FIG. 5, the frame 14 includes a back plate 20 and two side plates 22 and 24. The back plate 20 and side plates 22, 24 define a channel with an open front that surrounds and supports an elongated ultraviolet (UV) lamp 26, which may be a germicidal lamp, or a germicidal and ozone producing hybrid UV lamp, both of which are commercially available. An elongated reflector 28 is also supported by the frame 14 to reflect and focus radiation emitted from the lamp towards the open front of the frame 14. One end of the frame 14 is attached to the housing 16, and the other end of the frame 14 terminates in an end plate 30 (FIG. 2) to increase rigidity of the frame structure. As shown in FIG. 1, the housing 16 is a closed box structure with a top plate 32, a bottom plate 34, side walls 36, front wall 38 and back wall 40 (FIG. 2). The one end of the frame 14 is secured to the bottom plate 34 of the housing 16 in a perpendicular relation by spot welding, or any known mechanical fastener. An opening 42 (see FIG. 5) in the bottom plate 34 of the housing, is preferably sized and shaped to provide full access from the inside of the housing to the channel defined by the frame 14.

The ultraviolet lamp 26 is supported at opposite ends by a pair of lamp support members 44, the longitudinal axes of the lamp 26 and the frame 14 being parallel. Each lamp support member 44 is secured to support brackets 46,48 (see FIG. 2) which are secured to opposite ends of the back plate 20 of the frame 14. The support bracket 48 extends through the opening 42 into the housing 16 to provide a space between its remote end and the one end of the ultraviolet lamp 26 for a lamp socket 50, which provides a wiring connection to the ultraviolet lamp 26 for conducting electric current to energize the lamp. The lamp 26 and lamp socket 50 are preferably selected from a type in which one socket provides a full wiring connection to the lamp 26 at only one end thereof so that no wiring is required at the other end of the lamp 26. A dual socket lamp may also be used, however, in which case the electric conductors are routed behind the reflector 28. The wiring extends through and is supported by the bracket 48. Link arms 52 connect each end of the elongated reflector with respective tie plates 54,56. The tie plates 54 and 56 may be fixedly or rotatably mounted on the respective support brackets 46 and 48, depending on a shape of the reflector 28. The reflector 28 focuses the radiation emitted by the ultraviolet lamp 26, and also protects the lamp 26 from dust contamination by acting as an air foil that creates a slight vacuum around the lamp 26 to inhibit the collection of dust particles on the lamp.

If the reflector focuses the radiation over a wide, predefined area to be irradiated, the reflector is fixedly mounted to the frame. If, however, the reflector focuses the radiation in a narrow, concentrated band, the reflector is rotatably mounted to the frame so that the reflector 28 is rotatable about the longitudinal axis of the ultraviolet lamp 26. Thus, the radiation emitted by the lamp 26 and focused by the reflector 28 in a narrow, concentrated band is systematically swept over the predefined area as the reflector 28 is oscillated about a rear side of the ultraviolet lamp 26. The reflector 26 may be made from an aluminum alloy having a bright polished side to enhance reflection. Such sheet metal is available, for example, from Ideal Metal in Toronto, Canada and is identified as Aluminum Bright (1100-H24). The sheet metal is typically rolled into the desired shape using techniques well known in the art. Alternatively, the reflector may be molded from a plastic or powdered metal composition or extruded using a thermoplastic, for example. An inner surface of the reflector is then coated with a highly reflective coating, well known in the art. If the reflector 28 is shaped to focus the radiation in a narrow, concentrated band, the focal length of the reflector 26 is preferably such that the radiation emitted by the ultraviolet lamp 26 is most concentrated when the radiation is focused at the edges of the predefined area, so that the germicidal affect on the area is as consistent as possible.

If the reflector 28 is rotatably mounted to the frame 14, oscillation of the reflector 28 is preferably accomplished by a 24 volt twin coil gear reduction motor 58, well known in the art. The motor 58 drives a fly wheel 60 of a cam shaft assembly. The fly wheel 60 in turn moves an arm 62 of the cam shaft assembly which is connected to the tie plate 56 to oscillate the reflector 28. A similar structure for oscillating the reflector, which sweeps focused radiation over a predefined area is described in Applicant's U.S. Pat. No. 5,837,207, which is incorporated herein by reference.

The gear reduction motor 58 is mounted to the inner side of the top plate 32 of the housing 16 by fasteners (not shown) inserted through mounting bores 64 (see FIG. 5). The top plate 32 of the housing is detachably secured to the side walls 36 and the front and back walls 38, 40 by any well known mechanical means. The housing 16 also provides a base structure and room to support and contain other components therein. A ballast 66 and a terminal block 68 are affixed on the bottom plate 34 of the housing. A switch 70, indication lamp 72 and a fuse 74 with a protective bracket 76 are mounted to the top plate 32 of the housing. A power cord 78 with a three prong power plug 80 is attached to the top plate 32 of the housing and wired to the electric components. The function of those components and the wiring thereof will be described with reference to FIG. 7.

The mounting bracket 18 is separable from the housing 16 as shown in FIG. 3. The mounting brackcet 18 includes a front wall 82, a back wall 84, side walls 86 with a bottom plate 88, which only partially closes the bottom of the mounting bracket 18 to permit the elongated frame 14 to extend through the mounting bracket 18. The mounting bracket 18 is a rectangular box structure sized and shaped to receive the housing 16 therein and securely retain the elongated frame 14 in any orientation. The elongated frame 14 is locked in the mounting bracket 18 to ensure that the quick-install irradiation unit 10 can be mounted to a flat surface in any orientation. Any number of locking mechanisms can be used, including screw fasteners (not shown), for example. By way of example, a quick-release latch mechanism is illustrated and described. It should be understood, however, that other types of locking mechanisms have been contemplated and designed. The quick-release latch mechanism includes a latch member 90 pivotally mounted on the external side of the top plate 32 of the housing 16 to slide under a head of a locking pin 92, as shown in FIG. 4. The locking pin 92 is secured to the bottom plate 88 of the mounting bracket 18 and extends through openings 94 defined in the respective bottom plate 34 and top plate 32 of the housing 16 (only one opening in the top plate 32 is shown in FIG. 3) when the housing 16 is received within the mounting racket 18. The mounting bracket 18 includes two flanges 96 that extend outwardly from the bottom edge of the respective side walls 86 of the mounting bracket 18.

It is therefore convenient to mount the mounting bracket 18, when separated from the support structure 12, to a flat support surface in a desired position. When the elongated frame 14 extends through the mounting bracket 18 and the housing 16 is received in the mounting bracket 18, the elongated frame 14 is supported in proximity to a surface to be irradiated. The predefined area over which the focused radiation is directed by the unit should be coincident with the surface to be irradiated, so that the surface is exposed to germicidal levels of radiation. The lock mechanism, such as latch member 90 and the locking pin 92, ensures that the housing 16 is securely seated in the mounting bracket 18 and the elongated frame 14 is supported in its position with respect to the surface to be irradiated, regardless of the orientation of the irradiation unit 10 connected to the external structure. A handle 93 is provided on the top plate 32 of the housing 16 so that it is convenient to handle and carry the germicidal irradiation unit. Examples of applications of the invention will be further described below with reference to the drawings of FIGS. 8 and 9.

FIG. 6 illustrates an alternate arrangement for focusing the ultraviolet radiation emitted by the ultraviolet lamp 26. In this embodiment, the reflector 98 reflects ultraviolet radiation onto a convex lens 100 which focuses the ultraviolet radiation in much the same way as a focused reflector 28 described above. The lens 100 may be made from, for example, a UV resistant and transmissive acrylate or Teflon plastic, quartz or a UV transmissive glass used in the manufacture of UV lamps. The lens 100 is preferably configured to have a focal length such that the radiation emitted by the ultraviolet lamp 26 is most concentrated when the radiation is focused at the edges of the predefined area. The lens 100 also further protects the ultraviolet lamp 26 from exposure to dust particles suspended in the air.

Figure 7:
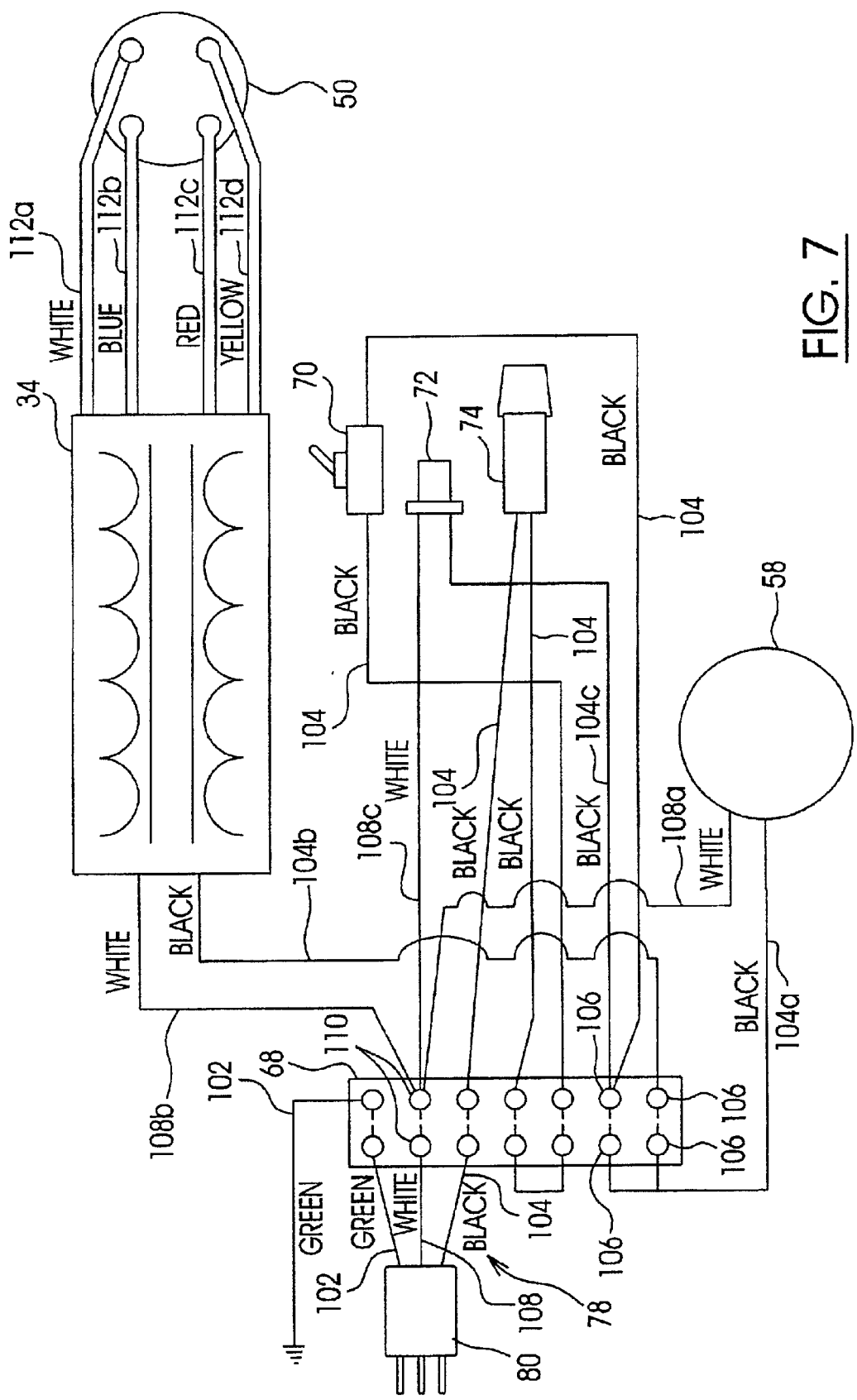
FIG. 7 is a wiring diagram suitable for a germicidal irradiation unit in accordance with the invention.

FIG. 7 is a wiring diagram suitable for wiring the quick-install irradiation unit 10 in accordance with the invention. The three prong power plug 80 is connected to the power cord 78, which typically supplies 120 VAC input current. A ground conductor 102 of the power cord 78 is connected to ground through the terminal block 68. A power conductor 104 of the power cord 78 connected through the terminal 68 is interrupted by the fuse 74 and the switch 70, and terminated at one of the connecting points 106 of the terminal block 68, which points are interconnected together to serve as a high voltage end in the circuit when the switch 70 is in an "on" position. A conductor 108 of the power cord 78 is connected to the connecting points 110 of the terminal block 68, which serve as a low voltage end in the circuit. The gear reduction motor 58 is connected through the conductor 104a to the high voltage end connecting points 106 on the terminal block 68, and connected through the conductor 108a to the low voltage end connecting points 110 on the terminal block 68. The gear reduction motor is thus energized by electric current when the switch 70 is on. Similarly, conductors 104b and 108b interconnect the ballast 34 and the respective connecting points 106 and 110 to supply 120 volt AC input to the ballast 34, which is connected to the lamp socket 50 by conductors 112a, 112b, 112c and 112d. The ballast 34 transforms the 120 volt AC input to a voltage output suitable for driving the ultraviolet lamp 26. The indication lamp 72 is also connected through conductors 104c and 108c to the respective high voltage end connecting points 106 and low voltage end connecting points 110 so that the indication lamp is illuminated to indicate an operation condition of the unit when the switch 70 is on and the fuse 74 works properly. A colouring system is indicated in FIG. 7 in which the black indicates the wiring with the high voltage end, the white with the low voltage end, and the green for ground. Yellow, red and blue colours are used to identify the wiring to the socket 50.

Figure 8:
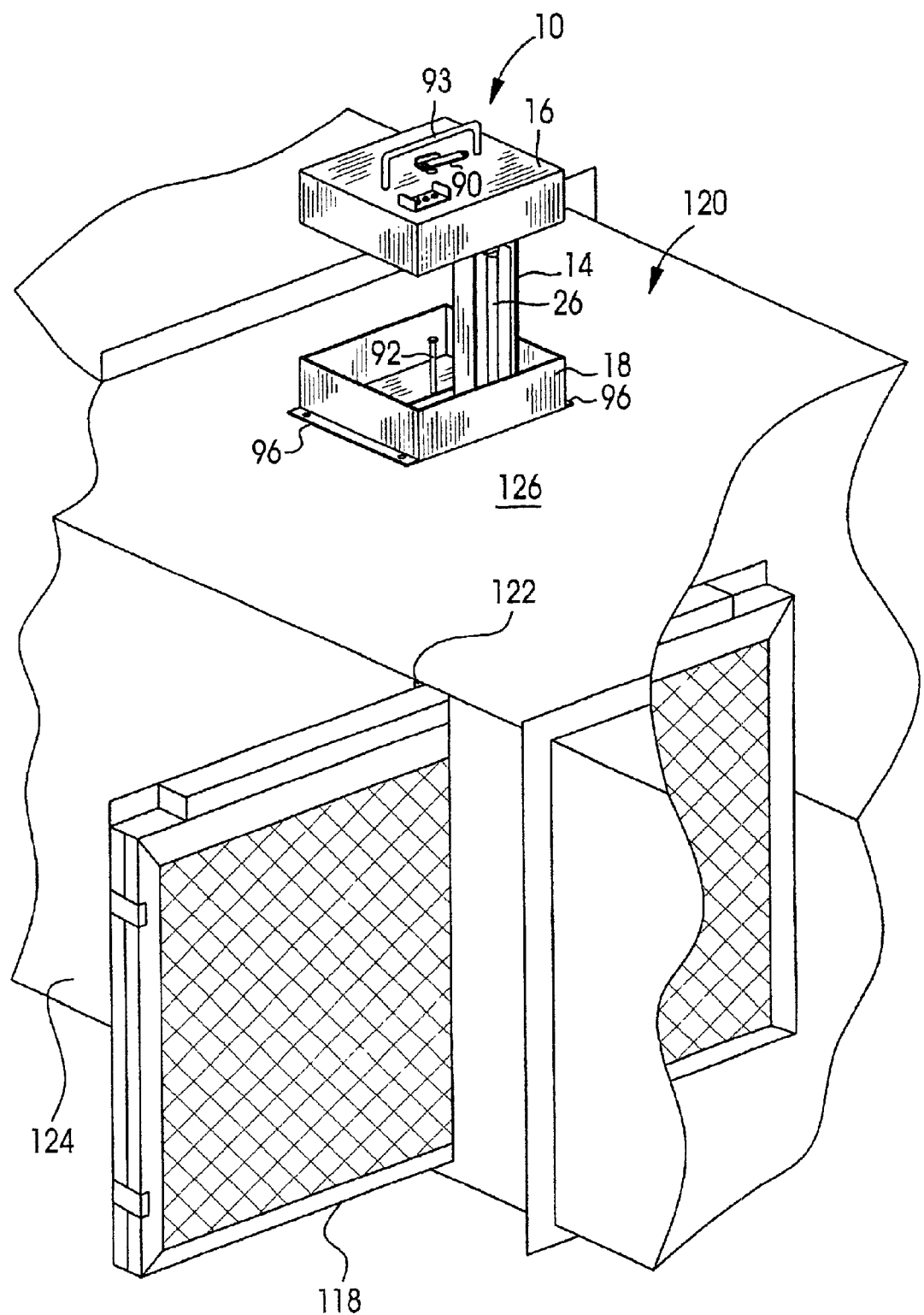
FIG. 8 is a perspective view showing an application of the invention in which the embodiment shown in FIG. 1 is installed in a vertical position in an air duct for irradiating an air filter pad inserted in the duct.

The quick-install irradiation unit 10 can be easily and conveniently installed to a support structure in proximity of a surface to be irradiated. For example, the unit can be quickly installed in an air duct, attached to an air conditioning or refrigeration unit to irradiate the coils where growth of micro-organisms is supported. An example of such an application of the invention is shown in FIG. 8. An air duct 120 is typically used in a forced-air heating system. An electrostatic air filter 118 may be inserted through a slot 122 in a side wall 124 of the air duct 120 to remove particulate matter suspended in the air when the air is drawn through the air duct 120. Microorganisms are collected with the particulate matter on the upstream side of the filter pad 118. It is convenient to install the germicidal irradiation unit 10 described above in the air duct 120 to expose the upstream side of the electrostatic air filter 118 to germicidal levels of radiation. The installation begins by cutting an aperture in a top wall 126 of the air duct 120, shaped and sized to permit the elongated frame 14 to be inserted down through the aperture into the air duct 120. The next step is to mount the mounting bracket 18 on the external side of the top wall 126, using fasteners to attach the flanges 96 to the top wall 126. The open portion of the bottom of the mounting bracket 18 is aligned with the aperture made in the top wall 126. The elongated frame 14 is inserted through the aperture in the top wall 126 into the air duct 120 until the housing 16 is seated in the mounting bracket 18. The latch member 90 is then rotated to slide under the head of the locking pin 92 to secure the unit in place.

The position of the aperture made in the top wall 126 of the air duct 120 should be carefully determined so that when the germicidal irradiation unit is installed, the elongated frame 14 is located in proximity to the upstream side of the filter pad 118. More especially, the distance between the ultraviolet lamp 26 of the unit and the upstream side of the filter pad 118 is determined so that the focused radiation emitted from the ultraviolet lamp 26 is focused on an entire area of the upstream side of the electrostatic air filter 118. If an oscillating reflector is used, the quick-install irradiation unit 10 should be positioned so that radiation is most concentrated when the radiation is focused at the edges of the upstream side of the electrostatic air filter 18.

Figure 9:
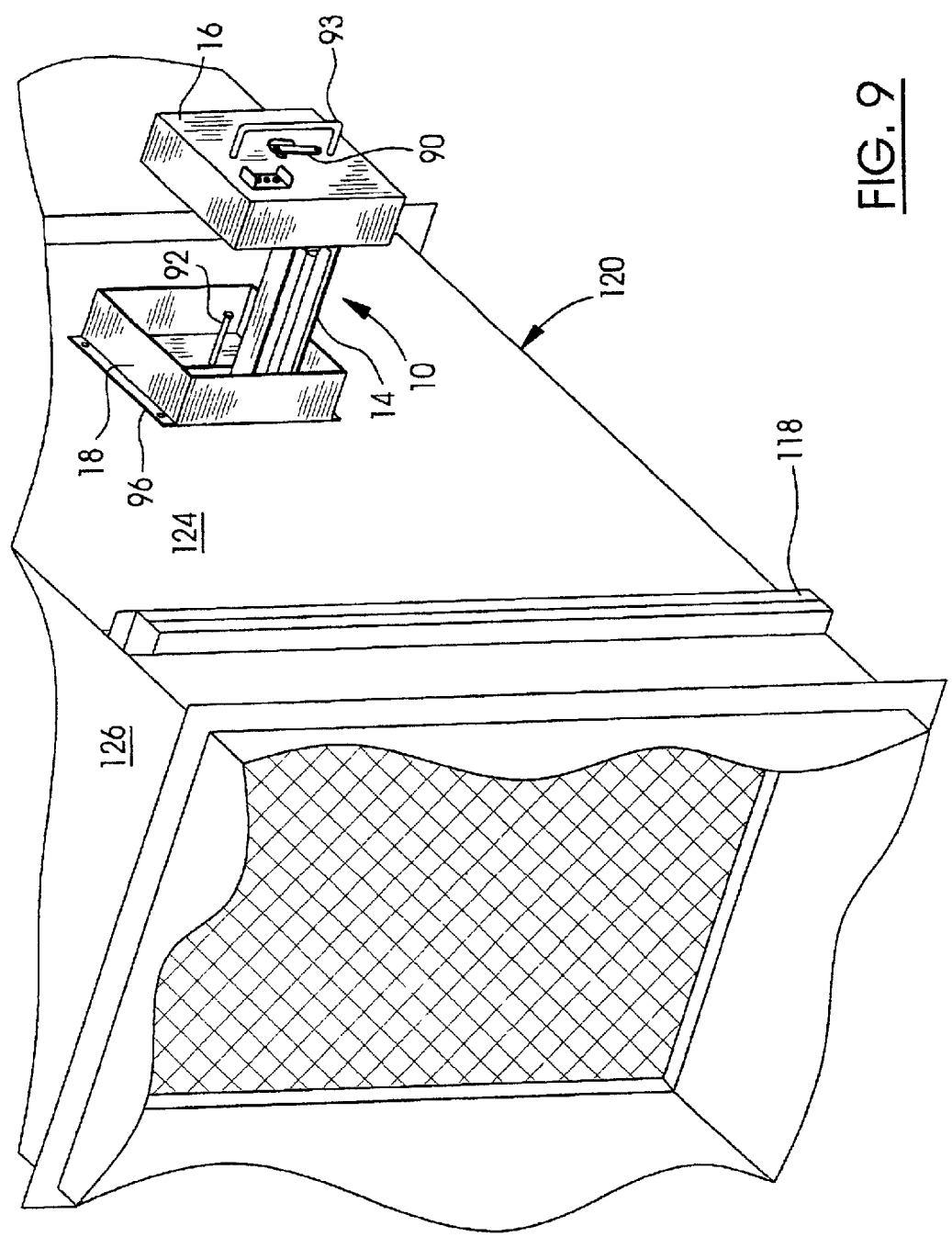
FIG. 9 is a perspective view, showing another application of the invention in which the embodiment shown in FIG. 1 is installed in a horizontal position in an air duct for irradiating an electrostatic air filter pad inserted in the duct.

FIG. 9 shows another example of an application of the invention. In this application, the quick-install irradiation unit 10 is installed in a horizontal position. The secure seating of the housing 16 in the mounting bracket 18 ensures that the elongated frame 14 is supported in its working position even though the unit is supported at the one end by the side wall 124 in a cantilevered orientation. The applications for the invention described with reference to FIGS. 8 and 9 are exemplary only, and the germicidal irradiation unit in accordance with the invention may be mounted to any suitable structure for irradiating a surface which benefits from irradiation.

The embodiment(s) of the invention described above is(are) intended to be exemplary only. The scope of the invention is therefore intended to be limited solely by the scope of the appended claims.

We claim:

1. A quick-install irradiation unit for irradiating a surface to be irradiated, comprising:
    a frame for supporting a radiation source and a means for focusing radiation emitted by the radiation source, the frame being configured to be mountable at only one end thereof; and
    a mounting bracket for receiving the one end of the frame for mounting the frame to a flat support surface, so that a radiation source mounted to the frame is supported in proximity to the surface to be irradiated and radiation emitted by the radiation source is focused on the surface to be irradiated by the means for focusing, the mounting bracket being mountable to a structure supporting the surface to be irradiated, the mounting bracket detachably securing the one end of the frame to maintain a longitudinal axis of the frame in a fixed relationship with the surface to be irradiated, regardless of an orientation of the quick-install irradiation unit, the elongated support frame comprises a housing at the one end, the housing being receivable in an open end of the mounting bracket and releasably locked therein.

2. A quick-install irradiation unit as claimed in claim 1 wherein the radiation source is supported between respective ends of the elongated support frame, and the means for focusing the radiation is supported between respective ends of the elongated support frame and reciprocally moveable about the source relative to the support frame, so that the radiation is focused in a narrow band that is systematically swept over the surface to expose the surface to radiation.

3. A quick-install irradiation unit as claimed in claim 2 wherein the means for focusing is reciprocally moved by a gear reduction motor and a cam assembly supported by the housing and operatively connected to the means for focusing.

4. A quick-install irradiation unit as claimed in claim 2 wherein the means for focusing the radiation comprises an elongated reflector.

5. A quick-install irradiation unit as claimed in claim 2 wherein the means for focusing the radiation comprises a reflector and a elongated lens.

6. A quick-install irradiation unit as claimed in claim 2 wherein the radiation source comprises an ultraviolet lamp.

7. A quick-install irradiation unit as claimed in claim 6 wherein the ultraviolet lamp is a germicidal/ozone producing lamp.

8. A quick-install irradiation unit for irradiating a surface that collects or supports growth of micro-organisms, comprising:
    an elongated frame and a housing secured to one end of the frame;
    a mounting bracket adapted to be mounted to a structure, and to receive the housing to support the elongated frame in proximity to the surface to be irradiated;
    an ultraviolet radiation source supported by the elongated frame for irradiating at least a portion of the sufface to be irradiated;
    a reflector for focusing the ultraviolet radiation emitted by the source, the reflector being rotatably motion to the frame;
    means for oscillating the reflector so that the surface is systematically exposed to germicidal levels of radiation; and
    means for detachably locking the housing to the mounting bracket to securely support the elongated frame in proximity to the surface to be irradiated, regardless of an orientation of the quick-install irradiation unit.

9. A quick-install irradiation unit as claimed in claim 8 wherein the ultraviolet radiation source comprises an elongated ultraviolet lamp wired only at one end thereof to an electric power source that is supported on the one end of the frame securing the housing.

10. A quick-install irradiation unit as claimed in claim 8 wherein the reflector has a polished side positioned next to the ultraviolet lamp.

11. A quick-install irradiation unit as claimed in claim 8 wherein the means for oscillating the reflector comprises a gear reduction motor and a cam assembly.

12. A method of making a quick-install irradiation unit mountable to a flat support surface in any orientation, comprising steps of:
   a) constructing a box-shaped mounting bracket having an open top end and mounting flanges that extend from at least two opposed side edges for mounting the mounting bracket to the flat support surface;
   b) constructing an elongated support frame having a housing at one end and a frame structure supported by the housing, the frame structure supporting a reflector for supporting an elongated ultraviolet lamp in front of the reflector, and the housing being sized to be closely received in the open top end of the mounting bracket; and
   c) constructing a mechanism for interlocking the mounting bracket and the housing so that the housing is retained in the mounting bracket when the mechanism is in a locked position, regardless of an orientation of the mounting bracket.

13. A method as claimed in claim 12 wherein step c) comprises steps of: securing a locking pin to a bottom plate of the mounting bracket; forming aligned openings in the housing to receive the locking pin; and, securing a latch member to a pivotal mount on an external side of a top plate of the housing so that the latch member can be rotated to slide under a head of the locking pin.

14. A method as claimed in claim 12 further comprising a step of forming the reflector from a sheet of metal having a polished side.

15. A method as claimed in claim 12 further comprising a step of extruding the reflector, and coating an inner surface of the reflector with a reflective material.

16. A method as claimed in claim 12 further comprising a step of mounting the reflector to swivel brackets that permit the reflector to be oscillated around a rear side of the ultraviolet lamp and connecting a motor to a one of the swivel brackets to oscillate the reflector.

* * * * *